(12) United States Patent
Hibino et al.

(10) Patent No.: US 8,804,908 B2
(45) Date of Patent: Aug. 12, 2014

(54) MOBILE X-RAY APPARATUS

(75) Inventors: Atsushi Hibino, Tokyo (JP); Toshikazu Kita, Tokyo (JP); Tetsuji Sairaiji, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/977,812

(22) PCT Filed: Jan. 10, 2012

(86) PCT No.: PCT/JP2012/050265
§ 371 (c)(1),
(2), (4) Date: Jul. 1, 2013

(87) PCT Pub. No.: WO2012/098949
PCT Pub. Date: Jul. 26, 2012

(65) Prior Publication Data
US 2013/0287171 A1    Oct. 31, 2013

(30) Foreign Application Priority Data

Jan. 18, 2011    (JP) .................................. 2011-007815

(51) Int. Cl.
*H05G 1/64*    (2006.01)
*A61B 6/00*    (2006.01)

(52) U.S. Cl.
CPC ............... *A61B 6/587* (2013.01); *A61B 6/4405* (2013.01); *A61B 6/4452* (2013.01); *A61B 6/4441* (2013.01)
USPC ........................................... 378/98.5; 378/98

(58) Field of Classification Search
CPC ..... A61B 6/587; A61B 6/4441; A61B 6/5211
USPC ......................................... 378/98, 98.2, 98.5
See application file for complete search history.

(56) References Cited

U.S. PATENT DOCUMENTS 6,354,737 B1 *   3/2002   Hufe et al. .................... 378/205
2011/0075812 A1   3/2011   Takekoshi et al.

FOREIGN PATENT DOCUMENTS

| EP | 2092890 A1 * | 8/2009 |
|---|---|---|
| JP | A-9-298687 | 11/1997 |
| JP | A-2004-73353 | 3/2004 |
| JP | A-2007-236784 | 9/2007 |
| JP | A-2008-110164 | 5/2008 |
| JP | B2-450326 | 7/2010 |
| JP | B2-4508326 | 7/2010 |
| JP | A-2011-67436 | 4/2011 |

OTHER PUBLICATIONS

International Search Report issued in International Patent Application No. PCT/JP2012/050265 dated Feb. 7, 2012.

* cited by examiner

*Primary Examiner* — Glen Kao
(74) *Attorney, Agent, or Firm* — Oliff PLC

(57) ABSTRACT

A mobile X-ray apparatus is provided with an X-ray source, an X-ray planar detector being arranged in such a manner as opposed to the X-ray source, a support (C-shaped arm) for linking and supporting the X-ray source and the X-ray planar detector, an angle input part for inputting a rotation angle at which the X-ray planar detector is rotated within a plane including the X-ray incidence plane, a rotation controller and a rotation mechanism for rotating the X-ray planar detector according to the rotation angle being inputted, an image generator for generating an image of the test subject based on the transmitted X-rays being detected, displays for displaying the image, and an image rotor for subjecting the image being displayed on the displays to a rotation process according to an amount of the rotation of the X-ray planar detector.

3 Claims, 5 Drawing Sheets

MOBILE X-RAY APPARATUS

TECHNICAL FIELD

The present invention relates to a mobile X-ray apparatus, and more particularly, it relates to a technique for aligning an X-ray detector having a rectangular-shaped X-ray incidence plane, which is typified by an FPD.

BACKGROUND ART

In recent years, a transition of an X-ray diagnostic imaging apparatus is currently in progress, from a type employing an image intensifier (hereinafter, abbreviated as "I.I.") as its X-ray detector, to a type employing a flat panel detector (hereinafter, abbreviate as "FPD"). This is because, the FPD facilitates reduction of a visual sense of oppression relative to the I.I., and the FPD has a wide dynamic range without distortion, enabling acquisition of favorable image quality.

The I.I. type mobile X-ray apparatus is still dominant, but currently the FPD type is being introduced into the market. Since it is expected that the FPD type is introduced more in the future, it becomes indispensable to address a technical problem which is caused by the mobile X-ray apparatus of the FPD type.

In the mobile X-ray apparatus, when a C-shaped arm supporting both X-ray radiographic equipment and the X-ray detector being arranged in such a manner as opposed to each other, places therebetween a portion of interest of a test subject (positioning the C-shaped arm with respect to the portion of interest is performed without interference with the test subject nor a bed on which the test subject is placed), since there are a wide variety of portions of interest and operative methods, variations are found such as a standing position of an operator and arrangements of peripheral equipment. Positioning of the mobile X-ray apparatus and an inserting direction of the C-shaped arm are required to be responsive to each of those variations. In other words, in many cases, the C-shaped arm is subjected to constraints that it has to be inserted from a position and in a direction so as not to be an obstacle to the operator and the peripheral equipment. One of the problems caused by the inserting direction is that the orientation of an image displayed on the display device, that is, the orientation of the portion of interest is not kept constant.

The operator carries out a diagnosis viewing the image displayed on the display device. Therefore, in order to avoid erroneous diagnosis and facilitate recognition of the portion of interest, it is necessary to display the portion of interest constantly in the same orientation within the X-ray image displayed on the display device (e.g., the body axis direction of the test subject is made to be in line with the longitudinal direction of the display, and the head of the portion of interest is made to be directed upward in the display), or it is alternatively necessary to display the portion of interest in a desired orientation.

However, the inserting direction of the C-shaped arm is different in each case, and also the portion of interest in the X-ray detector (X-ray incidence plane) supported by the C-shaped arm and the orientation thereof with reference to the body axis direction are different in each case. Therefore, in order to keep the portion of interest to be in the same orientation constantly, it is necessary to correct tilt of the portion of interest.

As a suggestion to address this problem, for example, the Patent Document 1 discloses a technique for mechanically correcting the rotation of a video system, such as a TV camera and TV deflection coil, in the I. I. type X-ray diagnostic apparatus. The Patent Document 2 discloses a technique for rotating the FPD to reserve a proper effective field of view, and also rotating the display device itself for displaying an image of the test subject, so as to allow the test subject to be in a desired orientation.

PRIOR ART DOCUMENT

Patent Document

Patent Document 1
  Japanese Unexamined Patent Application Publication No. 9-298687
Patent Document 2
  Japanese Patent No. 4508326

DISCLOSURE OF THE INVENTION

Problem to be Solved by the Invention

An X-ray diagnostic imaging apparatus of the FPD type does not include any mechanically rotatable portion of a video conversion system. Therefore, it is not possible to apply the technique as disclosed in the Patent Document 1 to the mobile X-ray apparatus. In the case where it is tried to produce a similar effect by image processing instead of the video conversion system, as for a circular-shaped image such as an image of the I. I., a display region of the display device stays the same i.e., unchangeable, even rotated in any direction, under the condition that the circular image is turned about the center of the circle. However, as for a rectangular image, simple rotation thereof may cause a part lying off the display region. Therefore, there is another method to display a part of the X-ray incidence plane of the rectangular-shaped FPD in a circular shape. However, this may cause a problem that it is not possible to effectively utilize the overall X-ray incidence plane of the FPD. On the other hand, it is also possible to reduce the image using a similar figure, so that displaying the whole image may not cause a part lying off the display region. However, there is also a problem that this results in displaying the portion of interest in a smaller size, and the image becomes hard to see for the operator.

In general, there is arranged peripheral equipment around the test subject, such as an infusion tube and various monitors. In the technique of the Patent Document 2, upon readjusting the positioning after trial imaging, the display device is rotated along with the rotation of the FPD, and therefore, there is a problem that the operator is required to check whether or not any of the FPD and the display device does not interfere with the peripheral equipment.

The present invention has been made in view of the problems above, and an object of the present invention is to provide a mobile X-ray apparatus which is able to perform positioning of the rotation, with carefully monitoring the X-ray planar detector during the rotation thereof.

Means to Solve the Problem

In order to solve the problems above, the mobile X-ray apparatus relating to the present invention is provided with, an X-ray source for irradiating a test subject with X-rays, an X-ray planar detector having an X-ray incidence plane for detecting transmitted X-rays through the test subject, a support for linking and supporting the X-ray source and the X-ray planar detector, arranging those elements in such a manner as opposed to each other, an angle input part for inputting a rotation angle at which the X-ray planar detector is rotated within a plane including the X-ray incidence plane, a detector rotor for rotating the X-ray planar detector according to the rotation angle being inputted, an image generator for generating an image of the test subject based on the transmitted X-rays being detected, a display for displaying the image, and an image rotor for subjecting the image being displayed to a rotation process according to an amount of the rotation of the X-ray planar detector.

Effect of the Invention

According to the present invention, when the X-ray planar detector is rotated after inputting a rotation angle, only the image being displayed is rotated at an angle corresponding to the amount of rotation of the X-ray planar detector, but the display device itself does not rotate. Therefore, it is possible to provide a mobile X-ray apparatus which allows positioning of the rotation, with carefully monitoring the X-ray planar detector during rotation thereof while checking whether or not the X-ray planar detector interferes with peripheral equipment.

BRIEF DESCRIPTION OF DRAWINGS

FIG. 5A illustrates an initial display state of the LIH image, FIG. 5B illustrates the state upon subjecting the LIH image to the rotation process, and FIG. 5C illustrates an X-ray image at the time of real imaging;

BEST MODE FOR CARRYING OUT THE INVENTION

Hereinafter, an embodiment of the present invention will be explained with reference to the accompanying drawings. It is to be noted that the same constituents shown in all the figures are labeled the same and tedious explanations will not be made.

Figure 1:
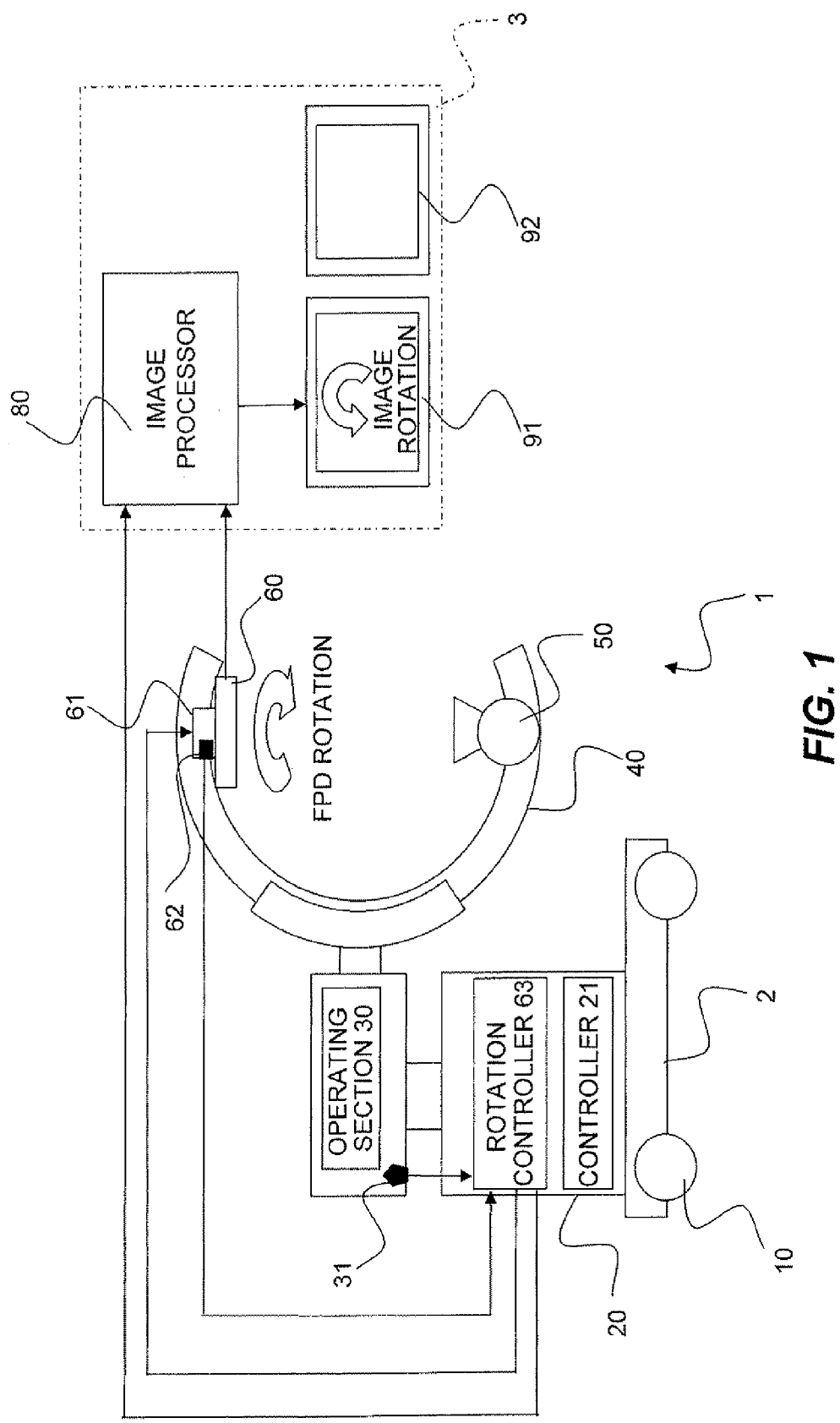
FIG. 1 is a block diagram showing a schematic configuration of the mobile X-ray apparatus 1 relating to the present embodiment.

Firstly, according to FIG. 1, a schematic configuration of the mobile X-ray apparatus relating to the present invention will be explained. FIG. 1 is a block diagram showing a schematic configuration of the mobile X-ray apparatus 1 relating to the present embodiment.

As shown in FIG. 1, the mobile X-ray apparatus 1 is provided with, broadly, a mobile X-ray supporting device 2 having an X-ray source 50 and an X-ray planar detector 60, and a mobile image processing device 3 having an image processor 80 and displays 91 and 92. The mobile X-ray supporting device 2 and the mobile image processing device 3 are configured separately, and wired or wireless electrical connection is established therebetween. In the present embodiment, an explanation will be made taking as an example, the mobile X-ray apparatus 1 incorporating the mobile X-ray supporting device 2 and the mobile image processing device 3 configured separately. However, this mobile X-ray apparatus may be configured in such a manner that the mobile X-ray supporting device 2 is equipped with the image display device in an integrated manner.

The mobile X-ray supporting device 2 is provided with a traveling section 10 having wheels, a main body 20 installed on the traveling section 10 and provided with a controller 21 for controlling X-ray radiation of the mobile X-ray apparatus 1 and also for controlling output processing of image signals from the X-ray planar detector 60, and an operating section 30 for accepting input operations by an operator, and a C-shaped arm 40 supported rotatably with respect to the main body 20, for linking and supporting the X-ray source 50 including an X-ray tube and the X-ray planar detector 60, arranging those elements in such a manner as opposed to each other.

The traveling section 10 travels, being equipped with the main body 20, the C-shaped arm 40, the X-ray source 50, and the X-ray planar detector 60.

In the present embodiment, an FPD having a rectangular-shaped X-ray incidence plane constitutes the X-ray planar detector 60, but it is not limited to the FPD, as far as there is an operational advantage of the present invention. In addition, the shape of the X-ray incidence plane may be a square type instead of the rectangular shape.

The X-ray planar detector 60 is connected to the C-shaped arm 40 via a rotation mechanism 61 which is supported rotatably with respect to the C-shaped arm 40. The rotation mechanism 61 is provided with an angle sensor 62 for detecting a rotation angle in the rotating plane according to the rotation mechanism 61.

The operating section 30 of the main body 20 is provided with an X-ray exposure switch not illustrated, and a device for inputting rotation angle of the X-ray planar detector 60, for example, an angle input button 31 being a rotary dial.

The main body 20 is further provided with a rotation controller 63 which receives an input signal indicating the rotation angle inputted from the angle input button 31, and outputs an instruction signal to the rotation mechanism 61 for carrying out the rotation at a rotation angle corresponding to the input signal. The angle input button 31 is a device for the operator to directly input the rotation angle of the X-ray planar detector, for example, being a device such as a dial switch or a device for inputting the rotation angle by tracing on a touch panel with the use of the operator's finger. The term "directly" is used here, so as to exclude an "indirect" input device which inputs the rotation angle of the X-ray planar detector via a rotation angle of a component other than the X-ray planar detector 60, for instance, so as to exclude the case where the rotation angle of the X-ray planar detector 60 is inputted via the rotation of a last image hold (hereinafter, abbreviated as "LIH") which will be described below.

The mobile image processing device 3 is provided with an image processor 80 for generating an X-ray image of the test subject, made up of a static image or a moving image, based on electric signals responding to the intensity of the transmitted X-rays through the test subject, being detected by the X-ray planar detector 60, and subjecting the image to a rotation process, and two displays 91 and 92 for displaying the X-ray image of the test subject, being generated by the image processor 80.

Each of the displays 91 and 92 is provided with a laterally-long rectangular-shaped image display region, and they are fixed on the mobile image processing device 3.

Figure 2:
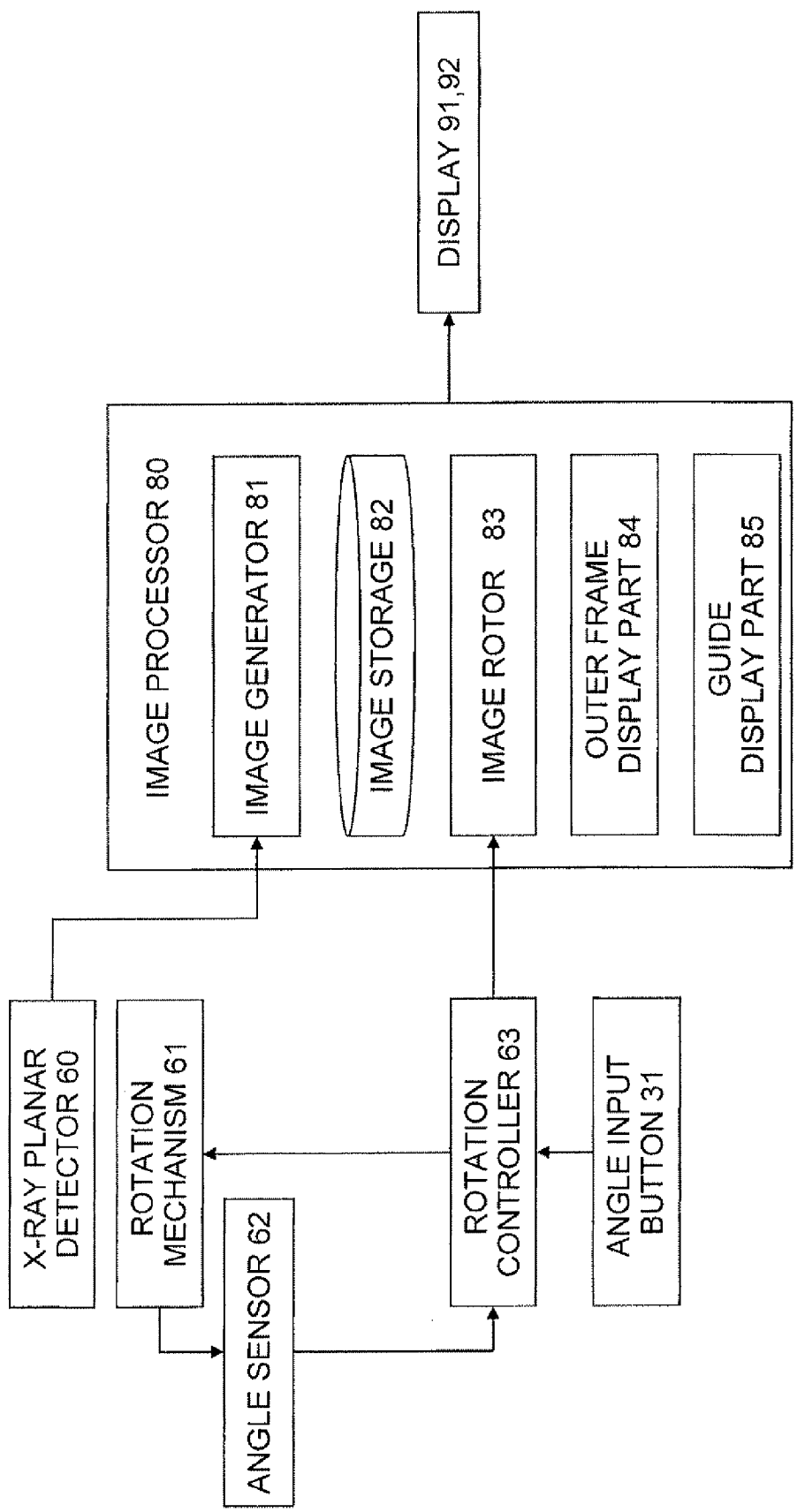
FIG. 2 is a block diagram showing a configuration of an image processor provided in the mobile X-ray apparatus 1 relating to the present embodiment.

Next, according to FIG. 2, an explanation will be made as to a configuration of the image processor 80. FIG. 2 is a block diagram showing the configuration of the image processor which is provided in the mobile X-ray apparatus 1 relating to the present embodiment.

The image processor 80 is provided with an image generator 81 for generating an X-ray image from the image signals based on the transmitted X-rays detected by the X-ray planar detector 60. The image processor 80 is provided with the image generator 81 for generating an image of the test subject made up of a static image or a moving image based on the transmitted X-rays through the test subject, an image storage 82 for recording the image generated by the image generator 81, an image rotor 83 for subjecting the image displayed on the display 91 or 92 to a rotation process according to the amount of rotation (corresponding to the rotation angle) of the X-ray planar detector 60, an outer frame display part 84 for storing coordinates of pixel positions of an image outer frame before the rotation process and displaying the image outer frame in a superimposed manner on the image after the rotation process, and a guide display part 85 for displaying a guide image indicating the rotation angle in a superimposed manner on the image being displayed. In the following, an explanation will be made taking as an example that the image generator 81 generates a static image by using a last image hold image (hereinafter abbreviated as "LIH image") of a moving image obtained by performing perspective imaging of the test subject, displays the LIH image on the display 91 or 92, and rotates the LIH image at the angle equivalent to the amount of the rotation of the X-ray planar detector 60. However, the image rotated along with the rotation of the X-ray planar detector 60 is not limited to the LIH image, but it may be a moving image obtained by fluoroscopy, or a static image obtained by photographing.

Upon detecting that the LIH image is displayed on the display 91 or 92, the rotation controller 63 outputs to the image rotor 83, an instruction signal to subject the LIH image being displayed to the rotation process, at the angle corresponding to the actual rotation angle of the X-ray planar detector 60 detected by the angle sensor 62. If any LIH image is not displayed on the display 91 and 92 (or it is not detected that the LIH image is displayed), the rotation controller 63 does not output the instruction signal as described above to the image rotor 83, even though the angle sensor 62 detects the actual rotation angle of the X-ray planar detector 60.

In the following, an explanation will be made taking as an example the case where the X-ray incidence plane of the X-ray planar detector 60 is positioned in such a manner as being laterally-long, with respect to the body axis direction of the portion of interest, and a rectangular-shaped X-ray image is displayed in the laterally-long rectangular-shaped image display region of the display 91. On this occasion, positioning of the X-ray planar detector 60 is performed, so as to take an image in which the body axis direction of the portion of interest imaged as the X-ray image is in line with the longitudinal direction of the image display region, and the head side of the portion of interest is located to be on the upper side of the image display region (hereinafter, referred to as a "normal image").

Figure 3:
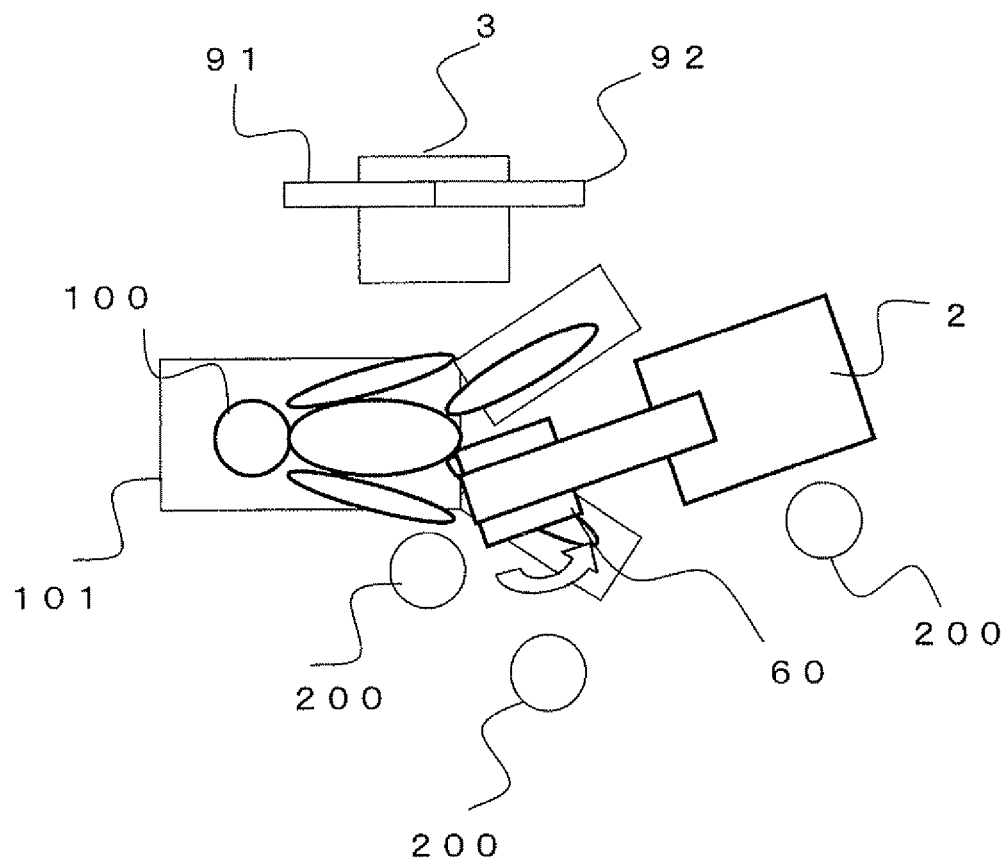
FIG. 3 illustrates an example of arrangement of the mobile X-ray apparatus 1 relating to the present embodiment.
Figure 4:
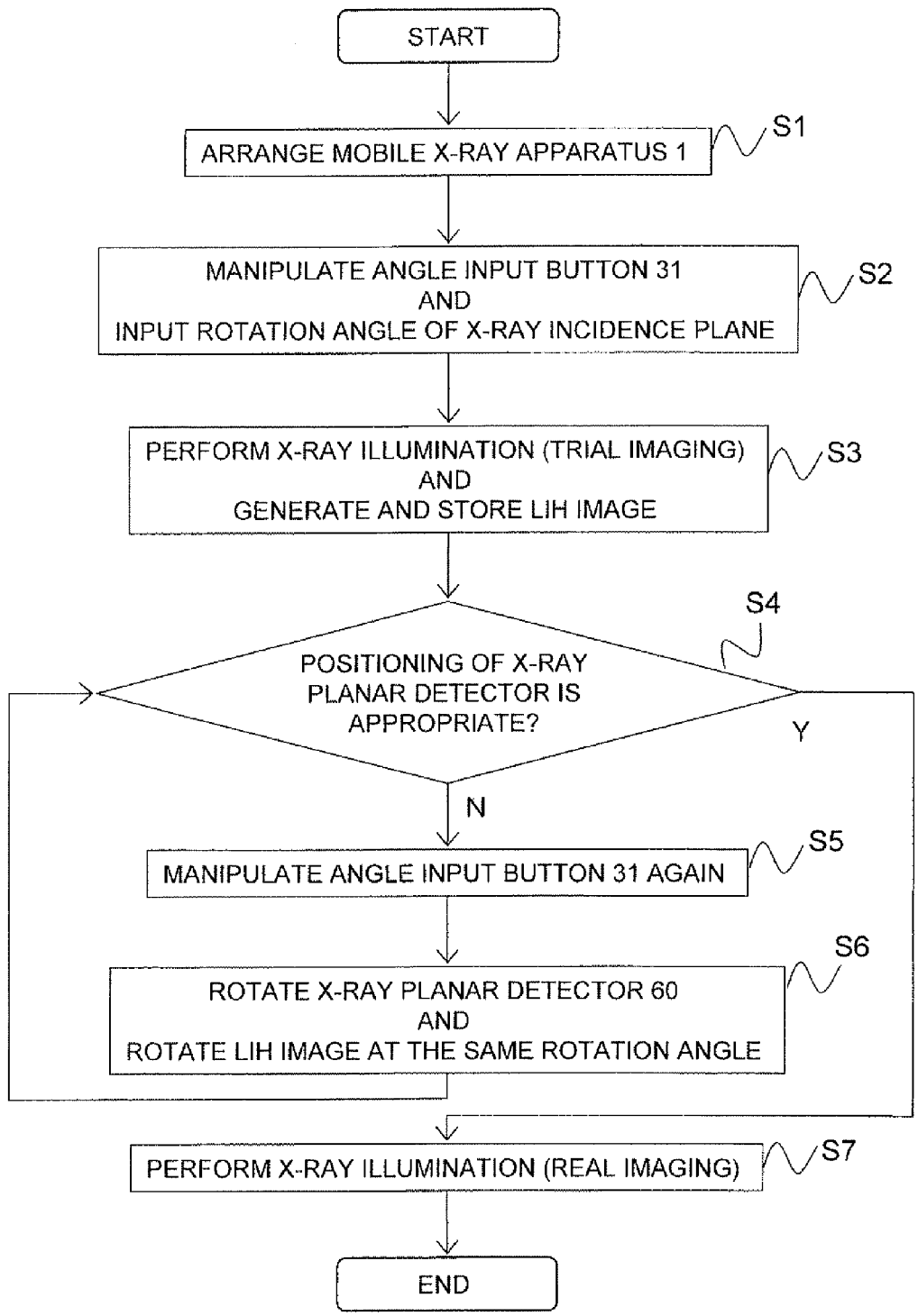
FIG. 4 is a flowchart showing a processing flow for arranging the mobile X-ray apparatus 1 relating to the present embodiment.
Figure 5A:
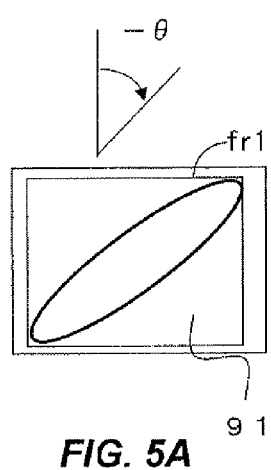
FIGS. 5A, 5B, and 5C illustrate a rotation process of an LIH image.
Figure 5B:
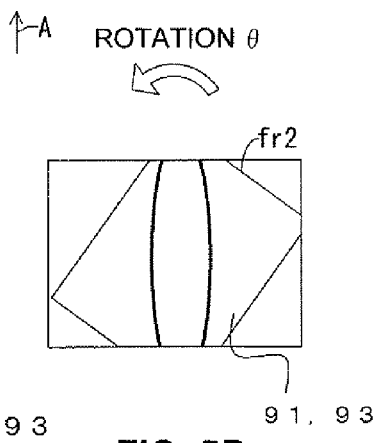
Figure 5C:
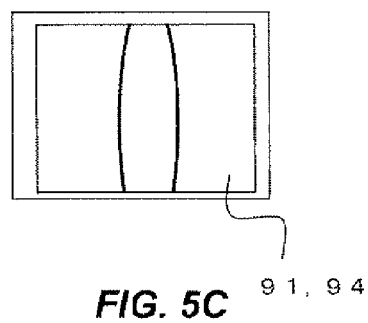
Figure 6:
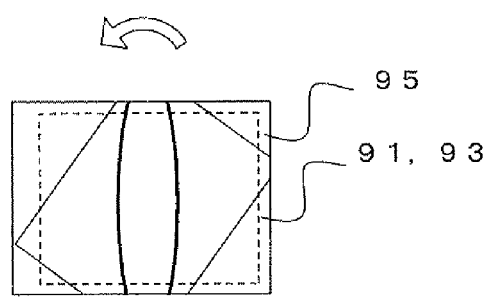
FIG. 6 illustrates the state where an outer frame of the LIH image at the time of initial display is displayed in a superimposed manner.
Figure 7:
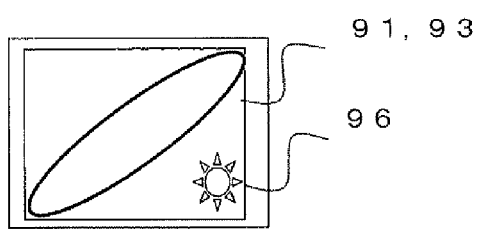
FIG. 7 illustrates the state where a guide image indicating a rotation angle is displayed in such a manner as superimposed on the LIH image at the time of initial display.

Next, with reference to FIG. 3 to FIG. 7, arrangement of the mobile X-ray apparatus 1 relating to the present embodiment will be explained. FIG. 3 illustrates an example of the arrangement of the mobile X-ray apparatus 1 relating to the present embodiment. FIG. 4 is a flowchart showing a processing flow for arranging the mobile X-ray apparatus 1 relating to the present embodiment. FIGS. 5A, 5B, and 5C illustrate the rotation process of an LIH image; FIG. 5A illustrates an initial display state of the LIH image, FIG. 5B illustrates the state upon subjecting the LIH image to the rotation process, and FIG. 5C illustrates an X-ray image at the time of real imaging. FIG. 6 illustrates the state where an outer frame of the LIH image at the time of initial display is displayed in a superimposed manner. FIG. 7 illustrates the state where a guide image indicating a rotation angle is displayed in a superimposed manner on the LIH image at the time of initial display. Hereinafter, an explanation will be made along each of the steps in FIG. 4.

(Step S1)

Firstly, the mobile X-ray apparatus 1 is moved from an equipment store room to an operating room, and it is placed at a position suitable for procedure. In the mobile X-ray apparatus 1 relating to the present embodiment, the mobile X-ray supporting device 2 and the mobile image processing device 3 are provided as separate devices, and thus, those elements are placed on appropriate positions, respectively (S1). In FIG. 3, it is assumed that the portion of interest of the test subject 100 placed on the bed 101 is the right leg, the mobile X-ray supporting device 2 is placed in proximity to the leg of the test subject 100, and the mobile image processing device 3 is placed in proximity to the left side of the test subject 100. Then, the operator 200 is positioned in such a manner as surrounding the bed 101. In general, the mobile X-ray supporting device 2 is arranged in such a manner that the X-ray source 50 is positioned below the test subject 100 and the X-ray planar detector 60 is positioned above the test subject 100.

(Step S2)

The operator manipulates the angle input button 31 to input a rotation angle indicating the rotation within the plane including the X-ray incidence plane of the X-ray planar detector 60 (S2). The rotation controller 63 outputs to the rotation mechanism 61, an instruction signal for instructing to perform the rotation according to the rotation angle that is inputted via the angle input button 31. In response to this instruction signal, the rotation mechanism 61 is rotated, and the rotation mechanism 61 allows the X-ray planar detector 60 to rotate. During the rotation, the operator carefully monitors whether or not the X-ray planar detector 60 interferes with the peripheral equipment. The angle sensor 62 detects the rotation angle of the X-ray planar detector 60, and transmits a detection signal to the rotation controller 63. In the present step, however, the rotation controller 63 detects that no LIH image is displayed on the display 91, and the process using this detection signal is not particularly performed.

(Step S3)

Next, in order to check whether or not the X-ray planar detector 60 is positioned appropriately, radioscopy is performed once (a trial imaging is performed) to determine the current position (S3). During the radioscopy, the image generator 81 receives image signals from the X-ray planar detector 60 and generates an X-ray image (radioscopic image). This X-ray image is displayed in real time on the display 91. When the radioscopy is stopped, the image generator 81 generates an LIH image made up of a static image, based on the radioscopic image, in particular, based on the image of the last frame, and displays the LIH image on the display 91, along with storing the LIH image in the image storage 82.

(Step S4)

The operator checks the LIH image, and determines whether or not the X-ray planar detector 60 exists at the position where a desired X-ray image is obtained (84). If the positioning of the X-ray planar detector 60 is performed with a high degree of precision in the step S2 and the portion of interest is imaged as a normal image on the LIH image, the next step is step S7. If the portion of interest is not imaged on the LIH image as a normal image, for example, the body axis direction of the portion of interest is inclined with respect to the longitudinal axis of the laterally-long X-ray image, or the head side of the portion of interest is directed downward in the image display region, the next step is step S5. By way of example, the LIH image 93 as shown in FIG. 5A is inclined at an angle −θ with respect to the longitudinal axis of the image display region, and it is not imaged as a normal image. Here, the outer frame fr1 in the state of laterally long in FIG. 5A fits into the laterally-long screen of the display 91.

(Step S5)

The operator manipulates the angle input button 31 again, so as to input the rotation angle of the X-ray planar detector 60 (55).

(Step S6)

The rotation controller 63 outputs to the rotation mechanism 61, an instruction signal for instructing the rotation according to the rotation angle inputted in the angle input button 31. In response to this instruction signal, the rotation mechanism 61 rotates the X-ray planar detector 60. During the rotation, the operator carefully monitors whether or not the X-ray planar detector 60 interferes with the peripheral equipment.

When the X-ray planar detector 60 is rotated, the angle sensor 62 detects the rotation angle of the X-ray planar detector 60, and transmits a signal indicating this rotation angle to the rotation controller 63. The rotation controller 63 determines that an LIH image is displayed on the display 91, and transmits to the image rotor 83, an instruction signal for applying a rotation process to the LIH image being displayed, at an angle that is equal to the rotation angle indicated by the detection signal. The image rotor 83 reads the LIH image 93 from the image storage 82, rotates the LIH image 93 in real time at the rotation angle which is equal to the rotation angle of the X-ray planar detector 60, based on thus received signal indicating the rotation angle, and displays the updated image (S6). With reference to FIG. 5B, this rotating operation will be explained. FIG. 5B illustrates the LIH image 93 obtained by rotating the LIH image of FIG. 5A in such a manner that the body axis direction of the portion of interest becomes in line with the longitudinal direction of the display 91 (the arrow A in FIG. 5), and the head of the portion of interest is directed upward in the display 91 (in the direction of the arrow A). Since FIG. 5B illustrates the LIH image 93 obtained by rotating the LIH image 93 of FIG. 5A at the angle θ, the outer frame fr2 of the LIH image 93 is displayed in such a manner as inclined with respect to the laterally-long rectangular-shaped screen of the display 91. The operator returns the process to the step S4, checks again the LIH image 93 having been rotated, and determines whether or not the portion of interest is at a desired position. If further rotation is necessary, manipulation of the angle input button 31 (S5) and checking of the LIH image (S6) are repeated.

In the present embodiment, the image rotor 83 applies the rotation process to the LIH image based on the signal indicating the rotation angle detected by the angle sensor 62, thereby rotating the LIH mage in which the rotation angle with respect to the initial position of the actual X-ray planar detector 60 is reflected with a higher degree of precision. However, the embodiment of the present invention further includes a configuration which is not provided with the angle sensor 62. By way of example, the rotation mechanism 61 is configured with the use of a driving device which is able to detect a rotation angle, just like a stepping motor or its control driver, and the signal indicating the rotation angle obtained by the rotation controller 63 from the angle input button 31 is outputted to the rotation mechanism 61. Then, the rotation mechanism 61 rotates the X-ray planar detector 60. In addition, the rotation mechanism 61 may output a signal indicating an actual rotation angle to the image rotor 83, so as to allow the image rotor 83 to apply the rotation process to the LIH image. On this occasion, the LIH image is made to rotate at an angle equivalent to an angular amount of the rotation of the X-ray planar detector 60.

(Step S7)

When the radioscopy (real imaging) is performed, the X-ray image of the portion of interest is displayed, the X-ray image being taken in a desired position and orientation (in the present invention, the body-axis direction of the portion of interest is in line with the longitudinal direction, and the head of the portion of interest is directed upward in the laterally-long rectangular-shaped X-ray image) (S7). In the example of FIG. 5C, in the rectangular-shaped laterally-long X-ray image, a radioscopic image 94 is displayed in such a manner that the body-axis direction of the portion of interest is in line with the longitudinal direction of the rectangular-shaped laterally-long screen of the display 91, and the head of the portion of interest is positioned being directed upward in the X-ray image.

According to the present embodiment, after the positioning of the mobile X-ray supporting device 2, the rotation operation is performed via the angle input button 31 while viewing the X-ray planar detector 60, thereby allowing the positioning of the X-ray planar detector 60 with careful monitoring thereof so as to prevent interference with medical equipment installed surrounding the test subject 100. In addition, the LIH image is checked to verify whether or not positioning of the X-ray planar detector 60 is properly performed. If the positioning is not performed satisfactory, the angle input button 31 is manipulated again, thereby finely adjusting the position of the X-ray planar detector 60, and by rotating the LIH image, it is possible to check whether or not a desired image is obtained by the rotation.

As another embodiment, the outer frame display part 84 in the image processor 80 stores the coordinates of the outer frame fr1 at the time of initial displaying of the LIH image (corresponding to FIG. 5A). Then, as shown in FIG. 6, the outer frame 95 at the same position as the outer frame fr1 at the time of initial displaying (corresponding to FIG. 5A) may be displayed in such a manner as superimposed on the LIH image after the rotation (corresponding to FIG. 5B). Accordingly, even though the radioscopy is not performed again, it is possible to figure out easily the display range of the portion of interest after rotationally corrected, and this helps determination whether or not repositioning of the portion of interest is necessary.

In addition, as shown in FIG. 7, the guide display part 85 in the image processor 80 may display a guide image 96 being an indication of rotation angle, in such a manner as superimposed on the initial display of the LIH image 93 (corresponding to FIG. 5A), or the image after the rotation process (corresponding to FIG. 5B). Accordingly, this facilitates knowing how much more rotation is required at the time of checking the LIH image.

In the present embodiment, the angle input button 31 is placed in proximity to the operating section 30, but it may be provided on the C-shaped arm 40, or it is further possible to configure the angle input button 31 as a remote control separated from the main body 20. This configuration allows the operator standing just beside the test subject 100 to perform rotating operation of the X-ray planar detector 60, thereby reassuring the test subject 100 being anxious, and facilitating the positioning of the X-ray planar detector 60 while avoiding interfering with other medical equipment.

Moreover, in the present embodiment, positioning of the X-ray planar detector 60 is performed once (step S2 in FIG. 4), and thereafter the LIH image is checked (step S3 in FIG. 4), but it is alternatively possible that positioning of the X-ray planar detector 60 is skipped, so as to firstly check the LIH image (step S3 in FIG. 4), and then the angle input button 31 is manipulated. With this configuration, the initial operation for positioning the X-ray planar detector 60 is skipped, thereby simplifying the operation procedure. On the other hand, if the operator determines that positioning of the X-ray planar detector 60 is sufficiently precise, checking of the LIH image (step S3 in FIG. 4) may be skipped before the real imaging. Accordingly, ineffective exposure to radiation may be reduced, with simplifying the operation procedure.

The mobile X-ray apparatus 1 of the present invention applied to the aforementioned embodiment is provided with, an X-ray source (e.g., 50) for irradiating a test subject with X-rays, an X-ray planar detector (e.g., 60) having a rectangular-shaped X-ray incidence plane for detecting transmitted X-rays through the test subject, a support (e.g., the C-shaped arm 40) for linking and supporting the X-ray source (e.g., 50) and the X-ray planar detector (e.g., the X-ray planar detector 60) in such a manner that those elements are opposed to each other, an angle input part (e.g., the angle input button 31) for inputting a rotation angle for rotating the X-ray planar detector (e.g., 60) within a plane including the X-ray incidence plane, a detector rotor (e.g., the rotation mechanism 61 and the rotation controller 63) for rotating the X-ray planar detector according to the rotation angle being inputted, an image generator (e.g., 81) for generating an image of the test subject based on the transmitted X-rays being detected, a display (e.g., 91 or 92) for displaying the image, and an image rotor (e.g., 83) for subjecting the image being displayed to a rotation process, according to an amount of rotation of the X-ray planar detector. With this configuration, the rotation angle is inputted in advance, then the X-ray planar detector 60 is rotated, and only the image being displayed is rotated according to the amount of rotation of the X-ray planar detector 60. Therefore, during the rotation of the X-ray planar detector 60, it is possible to carefully monitor the X-ray planar detector 60 and avoid interference with the peripheral equipment.

Industrial Applicability

The present invention is not only applicable to the medical use, but also to a nondestructive testing device utilizing X-rays for industrial use.

Explanation of References
1 Mobile X-ray apparatus
2 Mobile X-ray supporting device
3 Mobile image processing device
20 Main body
30 Operating section
40 C-shaped arm
50 X-ray source
60 X-ray planar detector

What is claimed is:

1. A mobile X-ray apparatus comprising,
an X-ray source for irradiating a test subject with X-rays,
an X-ray planar detector having an X-ray incidence plane for detecting transmitted X-rays through the test subject,
a support for linking and supporting the X-ray source and the X-ray planar detector, arranging the X-ray source and the X-ray planar detector in such a manner as opposed to each other,
an angle input part for inputting a rotation angle at which the X-ray planar detector is rotated within a plane including the X-ray incidence plane,
a detector rotor for rotating the X-ray planar detector according to the rotation angle being inputted,
an image generator for generating an image of the test subject based on the transmitted X-rays being detected,
a display for displaying the image,
an image rotor for subjecting the image being displayed, to a rotation process according to an amount of the rotation of the X-ray planar detector, and
an outer frame display part for displaying an outer frame of the image before the rotation process is displayed, in such a manner as being superimposed on the image after the rotation process, the outer frame having a rectangular shape.

2. The mobile X-ray apparatus according to claim 1, further comprising a guide display part for displaying a guide image indicating the rotation angle, in such a manner as being superimposed on the image being displayed.

3. The mobile X-ray apparatus according to claim 1, wherein,
the image generator generates as the image, a static image based on a moving image that is obtained by perspective imaging of the test subject.

* * * * *